(12) United States Patent
Saab

(10) Patent No.: US 8,979,806 B2
(45) Date of Patent: Mar. 17, 2015

(54) MEDICAL DEVICE WITH ADJUSTABLE TISSUE INGROWTH CUFF

(76) Inventor: Mark A. Saab, Lowell, MA (US)

(*) Notice: Subject to any disclaimer, the term of this patent is extended or adjusted under 35 U.S.C. 154(b) by 158 days.

(21) Appl. No.: 12/924,869

(22) Filed: Oct. 7, 2010

(65) Prior Publication Data

US 2011/0125129 A1 May 26, 2011

Related U.S. Application Data

(62) Division of application No. 10/485,036, filed as application No. PCT/US02/23387 on Jul. 23, 2002, now Pat. No. 7,811,257.

(60) Provisional application No. 60/308,328, filed on Jul. 27, 2001.

(51) Int. Cl.
| | |
|---|---|
| *A61M 5/32* | (2006.01) |
| *A61M 25/18* | (2006.01) |
| *A61M 39/02* | (2006.01) |
| *A61M 1/28* | (2006.01) |

(52) U.S. Cl.
CPC ........... *A61M 39/0247* (2013.01); *A61M 1/285* (2013.01); *A61M 2039/0261* (2013.01); *A61M 2039/0273* (2013.01); *A61M 2039/0282* (2013.01); *A61M 2039/0285* (2013.01)
USPC .......................................... 604/175; 604/539

(58) Field of Classification Search
CPC .......................... A61M 39/02; A61M 39/0247
USPC ............. 604/175–180, 288–288.04, 533, 539
See application file for complete search history.

(56) References Cited

U.S. PATENT DOCUMENTS

| | | | |
|---|---|---|---|
| 3,663,965 A | 5/1972 | Lee et al. | |
| 3,752,162 A | 8/1973 | Newash | |
| 4,004,298 A | 1/1977 | Freed | |
| 4,134,402 A | 1/1979 | Mahurkar | |
| 4,266,999 A | 5/1981 | Baier | |
| 4,321,914 A | 3/1982 | Begovac et al. | |
| 4,327,722 A | 5/1982 | Groshong et al. | |
| 4,405,305 A | 9/1983 | Stephen et al. | |
| 4,488,877 A | 12/1984 | Klein et al. | |
| 4,578,063 A * | 3/1986 | Inman et al. | 604/175 |
| 4,583,968 A | 4/1986 | Mahurkar | |
| 4,634,422 A * | 1/1987 | Kantrowitz et al. | 604/539 |
| 4,654,033 A | 3/1987 | Lapeyre et al. | |

(Continued)

FOREIGN PATENT DOCUMENTS

WO 2007085907 A 8/2007

OTHER PUBLICATIONS

Raad, et al., Arch Internal Medicine, "Intravascular Catheter-Related Infections: New Horizons and Recent Advances", vol. 162, pp. 871-878, Apr. 2002.

(Continued)

*Primary Examiner* — Aarti B Berdichevsky
*Assistant Examiner* — Bradley Osinski
(74) *Attorney, Agent, or Firm* — David Silverstein; Onello & Mello, LLP.

(57) ABSTRACT

Methods and apparatus are disclosed for making and using adjustable epidermal tissue ingrowth cuff and catheter assemblies for transcutaneous placement to provide periodic or continuous external access for medical purposes to an interior body region of a patent who requires such medical treatment over an extended period of time.

34 Claims, 8 Drawing Sheets

(56) References Cited

U.S. PATENT DOCUMENTS

Figure 1:
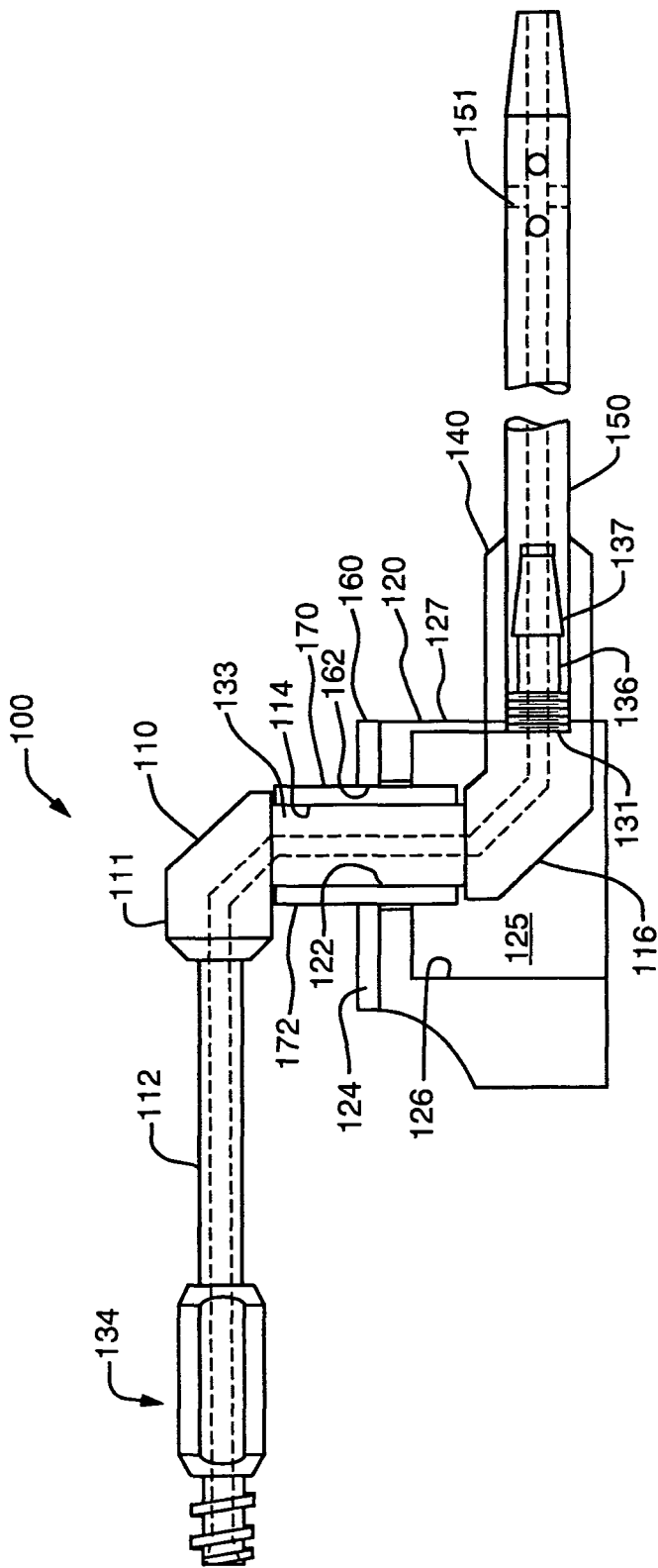

| | | | |
|---|---|---|---|
| 4,668,222 A | 5/1987 | Poirier | |
| 4,673,394 A | 6/1987 | Fenton, Jr. et al. | |
| 4,676,782 A | 6/1987 | Yamamoto et al. | |
| 4,808,155 A | 2/1989 | Mahurkar | |
| 4,886,502 A | 12/1989 | Poirier et al. | |
| 4,897,081 A | 1/1990 | Poirier et al. | |
| 4,898,669 A | 2/1990 | Tesio | |
| 4,935,004 A | 6/1990 | Cruz | |
| 4,959,054 A | 9/1990 | Heimke et al. | |
| 5,084,024 A | 1/1992 | Skinner | |
| 5,098,397 A | 3/1992 | Svensson et al. | |
| 5,100,392 A | 3/1992 | Orth et al. | |
| 5,156,597 A * | 10/1992 | Verreet et al. | 604/175 |
| 5,171,216 A * | 12/1992 | Dasse et al. | 604/43 |
| 5,242,415 A | 9/1993 | Kantrowitz et al. | |
| 5,556,381 A * | 9/1996 | Ensminger et al. | 604/288.03 |
| 5,562,618 A | 10/1996 | Cai et al. | |
| 5,624,392 A | 4/1997 | Saab | |
| 5,662,616 A | 9/1997 | Bousquet | |
| 5,685,878 A | 11/1997 | Falwell et al. | |
| 5,700,477 A | 12/1997 | Rosenthal et al. | |
| 5,718,678 A | 2/1998 | Fleming, III | |
| 5,718,692 A | 2/1998 | Schon et al. | |
| 5,743,873 A * | 4/1998 | Cai et al. | 604/288.02 |
| 5,766,249 A | 6/1998 | Griffith | |
| 5,776,111 A | 7/1998 | Tesio | |
| 5,823,994 A | 10/1998 | Sharkey et al. | |
| 5,830,184 A | 11/1998 | Basta | |
| 5,848,987 A | 12/1998 | Baudino et al. | |
| 5,882,341 A * | 3/1999 | Bousquet | 604/175 |
| 5,902,268 A | 5/1999 | Saab | |
| 5,947,953 A | 9/1999 | Ash et al. | |
| 5,989,213 A | 11/1999 | Maginot | |
| 6,033,382 A | 3/2000 | Basta | |
| 6,050,979 A | 4/2000 | Haemmerle et al. | |
| 6,099,508 A | 8/2000 | Bousquet | |
| 6,117,163 A | 9/2000 | Bierman | |
| 6,190,349 B1 | 2/2001 | Ash et al. | |
| 6,238,369 B1 | 5/2001 | Burbank et al. | |
| 6,264,673 B1 | 7/2001 | Egnelov et al. | |
| 6,355,020 B1 | 3/2002 | Bousquet | |
| 6,471,689 B1 * | 10/2002 | Joseph et al. | 604/892.1 |
| 6,520,949 B2 | 2/2003 | St. Germain | |
| 6,595,966 B2 | 7/2003 | Davey et al. | |
| 6,605,063 B2 | 8/2003 | Bousquet | |
| 6,638,242 B2 | 10/2003 | Wilson et al. | |
| 6,682,519 B1 | 1/2004 | Schon | |
| 6,695,832 B2 | 2/2004 | Schon et al. | |
| 6,719,724 B1 | 4/2004 | Walker et al. | |
| 6,719,749 B1 | 4/2004 | Schweikert et al. | |
| 6,872,198 B1 | 3/2005 | Wilson et al. | |
| 6,969,381 B2 | 11/2005 | Voorhees | |
| 7,014,623 B2 | 3/2006 | Prestidge et al. | |
| 7,018,374 B2 | 3/2006 | Schon et al. | |
| 7,811,257 B2 | 10/2010 | Saab | |
| 8,617,116 B2 | 12/2013 | Davey | |
| 2003/0229323 A1 | 12/2003 | Haarala et al. | |
| 2004/0181240 A1 | 9/2004 | Tseng et al. | |
| 2004/0204687 A1 | 10/2004 | Mogensen et al. | |
| 2004/0236314 A1 | 11/2004 | Saab | |
| 2005/0107753 A1 | 5/2005 | Rezai et al. | |
| 2005/0208095 A1 | 9/2005 | Hunter et al. | |
| 2006/0135946 A1 | 6/2006 | Moehle et al. | |
| 2006/0241737 A1 | 10/2006 | Tockman et al. | |
| 2007/0060891 A1 | 3/2007 | Skiera et al. | |
| 2007/0066966 A1 | 3/2007 | Davey | |
| 2007/0219510 A1 | 9/2007 | Zinn et al. | |
| 2007/0225642 A1 | 9/2007 | Houser et al. | |
| 2008/0140003 A1 | 6/2008 | Bei et al. | |
| 2009/0131919 A1 | 5/2009 | Davey | |

OTHER PUBLICATIONS

Fanous et al., "Dacron Implants in Rhinoplasty" Arch Facial Plast. Surg. vol. 4, Jul.-Sep. 2002, pp. 149-156.

* cited by examiner

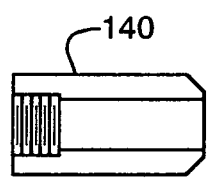
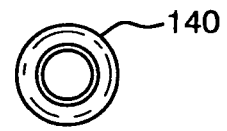
FIG. 4A    FIG. 4B
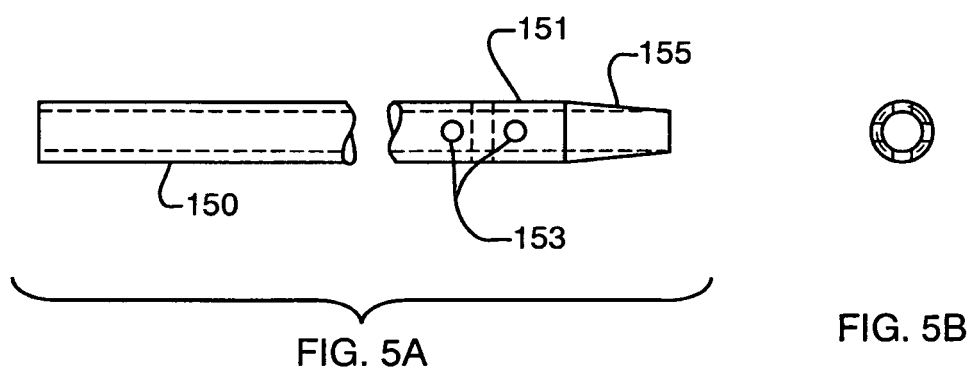
FIG. 5A    FIG. 5B

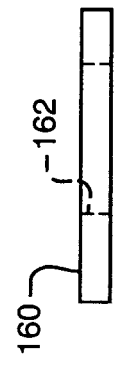
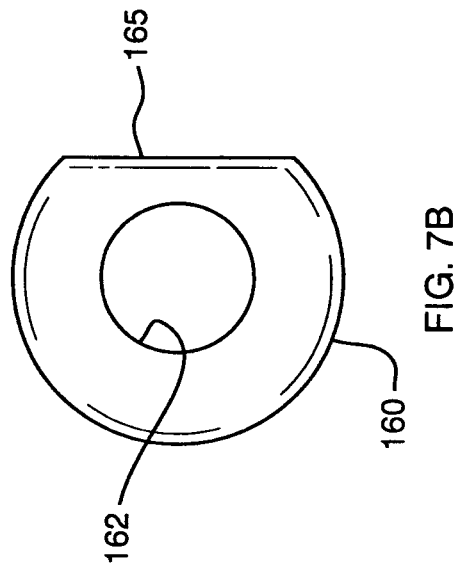
FIG. 7A
FIG. 7B
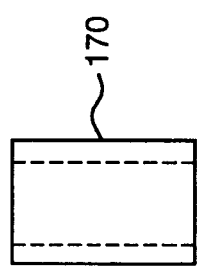
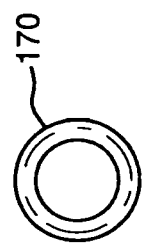
FIG. 6A
FIG. 6B

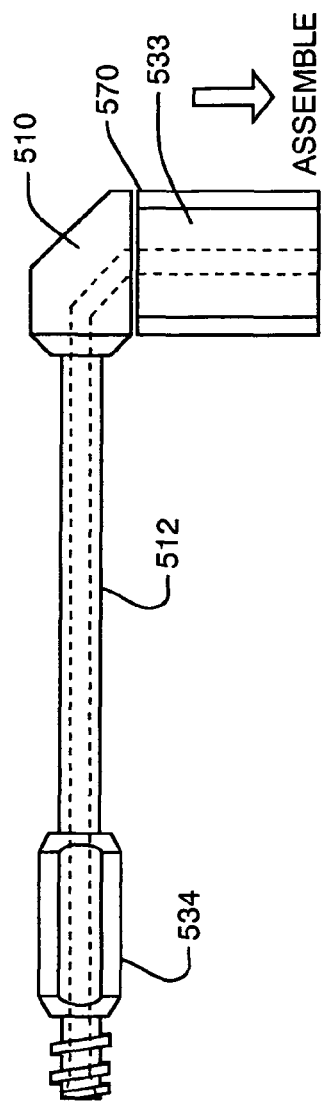
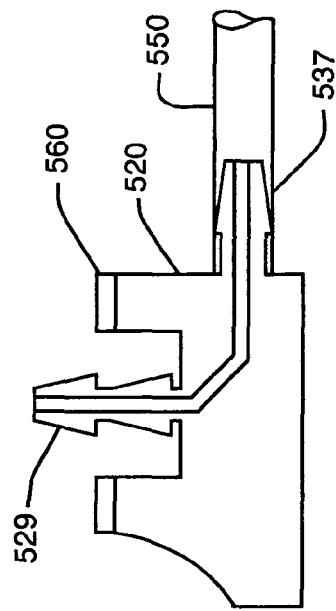
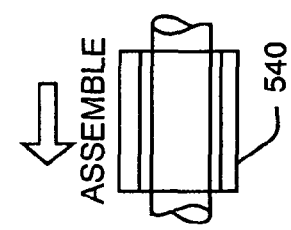
FIG. 9A
FIG. 9B
FIG. 9C

MEDICAL DEVICE WITH ADJUSTABLE TISSUE INGROWTH CUFF

CROSS-REFERENCE TO RELATED APPLICATIONS

This application is a Division of U.S. Ser. No. 10/485,036 filed Jan. 26, 2004 now U.S. Pat. No. 7,811,257, which claims benefit of the filing date of international application PCT/US02/23387 filed Jul. 23, 2002, which claims the benefit of the filing date of U.S. Provisional application Ser. No. 60/308,328 filed Jul. 27, 2001. The complete contents of these earlier applications are incorporated herein by reference.

FIELD OF THE INVENTION

The present invention relates generally to methods and apparatus whereby transcutaneously placed medical devices are used to provide periodic or continuous external access for medical purposes to an interior body region of a patient who requires such medical treatment over an extended period of time. The adjustable epidermal tissue ingrowth cuffs of the present invention can be adjustably coupled to a suitable catheter assembly in a way that facilitates positioning the catheter tip with a high degree of precision in order to deliver to and/or withdraw from a specific interior body site desired therapeutic or bodily fluids, which may alternatively comprise, for example, medication, normal saline, blood, wastes or in certain embodiments a contained heat exchange fluid, or to provide access to the internal body site for medical instruments.

BACKGROUND OF THE INVENTION

It is often necessary in medically treating a patient to establish long term vascular access to a specific desired interior body site for purposes of administering liquid therapeutic agents and/or for removing bodily fluids for testing/monitoring, for treatment before being returned to the body, or for disposal. In another increasingly common medical procedure, it is desired to deliver a contained heat exchange fluid at a temperature above or below normal body temperature to a specific interior body site for providing localized or general heating or cooling. In still other common medical procedures, such as angioplasty and laparoscopy, medical instrumentation is guided through a pre-positioned catheter line to a particular internal body location to monitor body conditions and/or to perform medical/surgical procedures.

Particularly in the case of administering fluids to, or removing fluids from, the body continuously or periodically over an extended time period, it is known in the medical arts to use what are known as "permanent" catheterization techniques employing subcutaneous-implanted devices such as tunneled central venous catheters (CVCs) for durations ranging from a few weeks to years. Examples of such subcutaneous-implanted and related medical devices are found in U.S. Pat. No. 4,266,999 (Baier); U.S. Pat. No. 4,405,305 (Stephen et al.); U.S. Pat. No. 4,488,877 (Klein et al.); U.S. Pat. No. 4,668,222 (Poirier); U.S. Pat. No. 4,897,081 (Poirier et al.); U.S. Pat. No. 4,935,004 (Cruz); U.S. Pat. No. 5,098,397 (Svensson et al.); U.S. Pat. No. 5,100,392 (Orth et al.); U.S. Pat. No. 5,242,415 (Kantrowitz et al.); U.S. Pat. No. 5,662,616 (Bousquet); U.S. Pat. No. 5,823,994 (Sharkey et al.); U.S. Pat. No. 5,830,184 (Basta); U.S. Pat. No. 5,848,987 (Baudino et al.); U.S. Pat. No. 5,882,341 (Bousquet); U.S. Pat. No. 5,989,213 (Maginot); and U.S. Pat. No. 6,033,382 (Basta), each of which is incorporated herein by reference. Examples of therapeutic regimens requiring such long term continuous or periodic access to a specific internal body location include parenteral feeding, chemotherapy, antibiotic administration, dialysis, and others.

Generally, the length of time the patient will be catheterized dictates whether a physician will utilize a "temporary" catheterization technique (i.e., a technique in which the catheter is left in a blood vessel for a relatively short period of time such as a few minutes, hours, days, or weeks) or a "permanent" catheterization technique (i.e., a technique in which the catheter is left in a blood vessel for a relatively long period of time such a several months or indefinitely).

For example, a procedure in which a clot is aspirated from a blood vessel typically includes placing the catheter in the blood vessel for a relatively short period of time such as a few minutes to a few hours and then withdrawing the catheter once the clot has been removed. Therefore, when performing such an aspiration procedure, it is common for a physician to use the temporary catheterization technique to place the catheter in the blood vessel of the patient.

On the other hand, when a procedure is performed to effect hemodialysis, a physician may place a catheter in the blood vessel for a relatively long period of time. In particular, a patient suffering from kidney failure who is involved in a hemodialysis regimen typically requires a dialysis session three times per week for an indefinite period of time whereby extra fluid, chemicals, and wastes are removed from his/her body. A patient who is involved in such a hemodialysis regimen may need a catheter placed in his/her blood vessel for a relatively long period of time in order to provide a ready means for vascular access into his/her bloodstream over such relatively long period of time. See, for example, K. Atherikul et al., "Adequacy of Haemodialysis with Cuffed Central-Vein Catheters," in *Nephrology Dialysis Transplantation* (vol. 13, no. 3, March 1998), which article is incorporated herein by reference. This long term placement of the catheter for dialysis purposes may be desirable for a number of reasons.

First, a patient may have experienced progressive loss of other conventional long term vascular access possibilities such as surgically created arteriovenous fistulas. Accordingly, the long term placement of the catheter in the patient's blood vessel may be the best, or only, alternative for the patient as he/she proceeds with the hemodialysis regimen.

Additionally, the long term placement of the catheter in the patient's blood vessel may be desirable after initial creation of an arteriovenous fistula in the patient's body. In particular, it is desirable to provide a ready means for vascular access into the patient's bloodstream during a maturation period of the arteriovenous fistula. The maturation period allows the arteriovenous fistula to develop sufficiently so that it will function as a ready means for vascular access into the patient's bloodstream which may be safely punctured multiple times per week for hemodialysis. The length of time of this maturation period is typically on the order of several weeks (e.g., three weeks) to many months (e.g., six months). Therefore, when performing a hemodialysis procedure, it is common for a physician to use the permanent catheterization technique to place the catheter in the blood vessel of the patient.

These two catheterization techniques are significantly different with respect to their complexity and degree of invasiveness. For example, in the case of the temporary catheterization technique, it is common to insert a temporary catheter into a patient's blood vessel using a "direct puncture technique." This technique entails creating a small incision in a patient's skin with a scalpel directly over the blood vessel to be catheterized. A needle is then advanced through the skin incision and subcutaneous tissue and into the blood vessel.

Thereafter, a guidewire is advanced through the needle into the blood vessel and the needle is subsequently removed over the guidewire. Then, one or more tubular vessel dilators are used to widen the opening defined in the skin and subcutaneous tissue, and further to widen the opening defined in the blood vessel wall to a caliber similar to that of the temporary catheter. The temporary catheter is then advanced over the guidewire and into the blood vessel. Thereafter, the guidewire can be removed.

When the temporary catheterization technique is used, for example, during a clot aspiration procedure, two catheters are usually placed in the blood vessel of a patient. In particular, an outer catheter is usually placed within the blood vessel using the above described direct puncture technique so that its distal opening is located near the clot. Thereafter, an inner catheter having a smaller caliber relative to the outer catheter is advanced through a lumen of the outer catheter. While the inner catheter is positioned within the outer catheter, an aspiration vacuum is applied to the inner catheter with a syringe. If the size of the clot (or fragments thereof) are smaller than the inner diameter of the inner catheter, then the clot or clot fragments are drawn into and through the inner catheter thereby removing the clot from the blood vessel. If the size of the clot or clot fragments are larger than the inner diameter of the inner catheter, then the clot or clot fragments are drawn to a location adjacent to the distal orifice of the inner catheter. Subsequently, while the aspiration vacuum is still being applied, the inner catheter is withdrawn from the outer catheter thereby additionally withdrawing the larger clot or clot fragments from the outer catheter and the patient's blood vessel. Thereafter, the outer catheter remains temporarily in place within the blood vessel of the patient for subsequent injections of radiographic contrast for imaging purposes to determine the extent of clot remaining in the blood vessel as well as to determine if clot has migrated to another location within the blood vessel. The outer catheter, which remains temporarily in place in the blood vessel, provides a conduit for the inner catheter to be advanced back into the patient's blood vessel for additional aspiration attempts which are usually required for complete removal of the clot from the blood vessel.

If an outer catheter needs to be replaced during a clot aspiration procedure because of catheter malfunction, such replacement can be accomplished by advancing a guidewire through the lumen of the outer catheter and into the blood vessel. The existing outer catheter can then be removed over the guidewire to a location outside of the patient's body. Thereafter, a new outer catheter is placed in the patient's blood vessel by advancing the new outer catheter over the guidewire as discussed above.

In contrast to the temporary catheterization techniques, the permanent catheterization techniques typically entail inserting a "permanent" catheter into a patient's blood vessel using a "tunneled catheter technique." The tunneled catheter technique includes: (i) creating a first opening by making a small incision in a patient's skin with a scalpel directly over the blood vessel to be catheterized; (ii) puncturing the blood vessel at a location directly below the first opening by advancing a needle through the skin incision and subcutaneous tissue and into the blood vessel; (iii) advancing a guidewire through the needle into the blood vessel; (iv) removing the needle over the guidewire; (v) passing one or more tubular vessel dilators over the guidewire to widen the opening defined in the skin and subcutaneous tissue, and further to widen the opening defined in the blood vessel wall to a caliber similar to that of the tubular guide; (vi) advancing the tubular guide, or introducer sheath, over the guidewire and into the blood vessel; (vii) thereafter, creating a second opening in the patient's skin spaced apart at least several centimeters from the first opening; (viii) advancing a tunneling instrument from the second opening to the first opening so as to create a passageway, or tunnel, within the subcutaneous tissue under the skin between the first opening and the second opening; (ix) advancing a permanent catheter having a tissue ingrowth member attached to an outer surface thereof into the second opening and through the passageway such that a distal end of the permanent catheter is located adjacent the first opening; (x) inserting the distal end of the permanent catheter through the tubular guide member and into the blood vessel to be catheterized whereby the tissue ingrowth member is positioned in the subcutaneous tissue; (xi) removing the tubular guide member; and (xii) closing the first opening with a suture whereby the permanent catheter (a) is no longer exposed through the first opening, (b) extends for at least several centimeters under the patient's skin between the second opening and the location where the permanent catheter enters the blood vessel, and (c) extends out of the second opening so that a proximal end of the permanent catheter is located outside of the patient's body.

In contrast to the direct puncture catheter technique, the tunneled catheter technique results in the placement of a catheter in a patient's body in a manner which allows the catheter to remain more safely in the patient's body for a relatively long period of time. For example, a degree of safety is achieved by separating the following two openings by at least several centimeters: (i) the skin opening through which the catheter enters the patient's body, and (ii) the blood vessel opening through which the catheter enters the patient's vascular system. This safety feature increases the difficulty for microbes to migrate up the length of the catheter from the skin opening and cause infection in the patient.

In addition, another degree of safety is achieved by providing a tissue ingrowth member which is attached to and extends around an outer surface of the catheter. As the catheter is left in the subcutaneous tunnel over a period of time, the tissue ingrowth member becomes affixed to the subcutaneous tissue of the patient's body thereby providing a secure attachment of the catheter to the patient's body. Providing a secure attachment between the catheter and the patient's body reduces the likelihood that the catheter will be inadvertently removed or withdrawn from the patient's body. Moreover, since the subcutaneous tissue becomes attached to the tissue ingrowth member, a physical barrier is created between following two openings: (i) the skin opening through which the catheter enters the patient's body, and (ii) the blood vessel opening through which the catheter enters the patient's vascular system. This physical barrier further increases the difficulty for microbes to migrate up the length of the catheter from the skin opening and cause an infection in the patient. Since the tissue ingrowth member is not positioned at the skin opening, it has no effect on microbial migration and subsequent possible infection at the proximal end of the tunnel, which could lead to the need to remove the catheter prematurely.

While the tunneled catheter technique provides the significant advantage of allowing the catheter to remain safely in the patient's body for a relatively long period of time, there are also significant disadvantages of the tunneled catheter technique. In particular, current CVC designs seriously compromise the skin's ability to protect the body from infection. CVC-related infection is a serious health problem that significantly increases the morbidity rate and cost of catheter usage. All previous attempts to modify tunneled CVC designs to reduce infection have failed to significantly decrease this cost or the morbidity rate. The primary reason for the failure of conventional CVCs is that none of the modified versions effectively block the path of microorganisms through the skin and into the body. See, for example, C. Crosby et al., "Skin Antisepsis: Past, Present, and Future," *JVAD* (Journal of Vascular Access Devices) (Spring 2001), which article is incorporated herein by reference.

As discussed above, it has been recognized in certain classes of medical catheter devices, for instance peritoneal dialysis catheters, that promoting epidermal tissue growth around a cuff or lip of the device can provide advantages over conventional methods. This topic is well summarized in an article written by Poirier et al., published in 1986 in the periodical "Frontiers in Peritoneal Dialysis" titled "Elimination of Tunnel Infection," which article is incorporated herein by reference. The authors teach that the epidermis is both the body's natural barrier to infection and the habitat of the largest reservoir of microorganisms causing catheter-related infection. Trauma to the epidermis, such as the incision required for insertion of catheters into the body, sets in motion a series of physiological mechanisms designed to heal the trauma and to re-establish the skin's capacity to prevent infection. Insight into these natural mechanisms, and equipping catheters with cuff technology at the incision site to facilitate the successful completion of these natural defense mechanisms, has been demonstrated to be an effective strategy to reduce catheter-related morbidity as well as cost. The uses of such natural mechanisms are summarized in the an article written by Dasse et al. in the periodical "Advances in Peritoneal Dialysis" titled "A Polyurethane Percutaneous Device for Peritoneal Dialysis," which article is also incorporated herein by reference.

Polyester fabric, commonly referred to by its tradename Dacron™, is one biocompatible, porous bed material which has been found to encourage the growth of tissue and collagen on and around the fabric for tissue ingrowth purposes. Fabric pore size is the characteristic most often quantified to specify the fabric most suitable for a given application. Fabric thickness and surface treatment are secondary factors for selection. This subject has been discussed in many technical and clinical journals. Two such references are "The effect of fiber diameter and fiber spacing on soft tissue ingrowth into porous polyester fabrics" by Ferguson et al., and "The effect of fiber diameter and carbon coating treatment on the in vitro and in vivo cellular response to dacron fabric materials" by Hong et al., both presented at the 17$^{th}$ Annual Meeting for the Society for Biomaterials held in May of 1991, both of which published papers are incorporated herein by reference. Another good reference on this subject is "Tissue reaction to Dacron velour and titanium fibre mesh used for anchorage of percutaneous devices" by Paquay et al. published in 1996 in Volume 17 of the periodical "Biomaterials," which article is also incorporated herein by reference.

The tissue ingrowth cuff designs developed for peritoneal dialysis catheters, however, cannot be readily translated to tunneled CVCs. Unlike peritoneal catheters, tunneled CVCs need to have their tips placed in a very specific location, typically the Superior Vena Cava/Right Atrial Junction (SVC/RA), in order to function properly over many months. Interventional radiologists are acutely aware of the need for highly precise tip placement because they are most frequently called on to resolve CVC complications. See, for example, "Tip Location of Peripherally Inserted Central Catheters," *JVAD* (Summer 1998), which article is incorporated herein by reference. The clinical benefits of proper catheter tip placement are very clearly spelled out in the DOQI standards issued in 1998 for proper placement of hemodialysis catheters. With currently available technology, the ability to precisely position CVC tips in the SVC/RA is enabled largely by the freedom to adjust/position the cuff location anywhere within the subcutaneous tunnel length. Thus, current tunneled CVC products cannot use cuffs that need to be precisely located at the incision site without losing the flexibility needed to ensure that the catheter tip is positioned precisely at the desired internal body location. This fundamental design conflict has led those skilled in this art to conclude that it is not feasible to combine conventional tunneled CVCs with the fixed implantable cuff technology, such as those described in U.S. Pat. No. 5,662,616 (Bousquet). This problem has heretofore been neither anticipated nor in any way addressed by the literature or practice in this art.

It has now been found, however, that a CVC apparatus which includes an adjustable epidermal tissue ingrowth cuff assembly according to the present invention overcomes these problems and deficiencies of the prior art CVC devices. Specifically, the apparatus and methods of the present invention allow a physician to place a fixed epidermal tissue ingrowth cuff assembly within a skin incision site and, subsequently, to adjust the location of the distal (internal) tip of a catheter assembly associated with the tissue ingrowth cuff assembly to precisely position the catheter tip at the desired body site without disturbing, moving, or stressing the fixed tissue ingrowth cuff.

OBJECTS OF THE INVENTION

Accordingly, a general object of the present invention is to provide adjustable epidermal tissue ingrowth cuff assemblies and methods of using them.

Another general object of the present invention is to provide one-piece or multiple-piece adjustable epidermal tissue ingrowth cuff assemblies to accommodate alternative therapeutic needs.

Still another general object of the present invention is to provide novel tunneled catheter/cuff assemblies that allow a user to place a fixed epidermal tissue ingrowth cuff within a skin incision site without hindering a physician's ability to thereafter adjust the location of the distal tip of an associated catheter shaft so as to locate the catheter tip at the optimum internal body location.

Still another general object of the present invention is to provide simplified and less costly tunneled CVC/tissue ingrowth cuff assemblies and associated methods for the placement of a catheter tip at a specific desired internal body location.

Yet another general object of the present invention is to provide epidermal tissue ingrowth cuff assemblies that minimize the discomfort experienced by a patient fitted with such a device.

A specific object of the present invention is to provide novel CVC/cuff assemblies that combine an adjustable epidermal tissue ingrowth cuff element with an associated adjustable catheter component to facilitate adjusting the length of the catheter portion inside the body distal of the body site where the epidermal tissue ingrowth cuff is implanted.

Another specific object of the present invention is to provide more cost-effective methods and apparatus for precisely locating and adjusting the distal end of the internal catheter portion of a CVC assembly inside a body.

Still another specific object of the present invention is to provide novel tunneled CVC/cuff assemblies that reduce the risk and incidence of infection originating at the incision site.

Other objects and advantages of the present invention will in part be obvious and will in part appear hereinafter. The invention accordingly comprises, but is not limited to, the apparatus and related methods, involving the several steps and the various components, and the relation and order of one or more such steps and components with respect to each of the others, as exemplified by the following description and the accompanying drawings. Various modifications of and variations on the apparatus and methods as herein described will be apparent to those skilled in the art, and all such modifications and variations are considered within the scope of the invention.

SUMMARY OF THE INVENTION

Eliminating the path microbes use to enter the body is the key to reducing CVC cost and morbidity associated with infection. The present invention provides for a device having a tissue ingrowth cuff assembly that can be placed at a fixed location at the incision site in combination with a catheter component which can be subcutaneously attached to the cuff assembly in such a way that its length and tip position is not constrained by the choice of cuff location. All exterior device surfaces that will reside above the skin are hermetically sealed by careful manufacturing processes. All surfaces that require assembly during device placement are designed to reside under the skin. The novel assembly of the present invention eliminates the principal and most common path for microbial migration from the skin surface to the interior of the patient via the percutaneous entry site.

In a first broad embodiment of this invention, the invention comprises a medical apparatus for establishing a long-term body access channel sealed along its length and extending from a proximal location outside the skin, through the epidermis, and into a living body where the channel is or can be subcutaneously connected to the proximal end of an implanted subcutaneous catheter after the proximal end is trimmed to size such that the distal tip of the subcutaneous catheter can be sited precisely at a desired internal body location, wherein the apparatus comprises:

(a) a hub component designed to be implanted subcutaneously, said hub component comprising an epidermal face along the exterior of a first hub wall portion, an epidermal face inlet in said epidermal face extending into a hub interior region, a hub outlet from the hub interior region along a second hub wall portion, and a hub passageway through the hub interior extending between the epidermal face inlet and the hub outlet;
  (b) at least a channel running seriatim from outside the body, through the epidermis, through the epidermal face inlet, and through the hub interior to the hub outlet when said hub component is implanted; and,
  (c) a hub outlet connector fitting at the distal end of the channel to provide a connection to the trimmed-to-size proximal end of an implanted subcutaneous catheter.

In a second broad embodiment of this invention, the invention comprises a method for establishing a long-term body access channel sealed along its length and extending from a proximal location outside the skin, through the epidermis, and into a living body where the channel is or can be subcutaneously connected to a proximal end of an implanted subcutaneous catheter after the proximal end is trimmed to size such that the distal tip of the subcutaneous catheter can be sited precisely at a desired internal body location, wherein the method comprises the steps of:

(a) subcutaneously implanting a fluid connection assembly comprising a hub component having an epidermal face along the exterior of a first hub wall portion, an epidermal face inlet in the epidermal face extending into a hub interior region, a hub outlet from the hub interior region along a second hub wall portion, and a hub passageway through the hub interior extending between the epidermal face inlet and the hub outlet;
  (b) determining the distance from said hub outlet to the desired internal body location;
  (c) providing at least a channel running seriatim from outside the body, through the epidermis, through the epidermal face inlet, and through the hub interior to the hub outlet and a hub outlet connector fitting at the distal end of the channel to provide a connection to a trimmed-to-size proximal end of an implanted subcutaneous catheter;
  (d) trimming the proximal length of the subcutaneous catheter as needed to mate the proximal end of the catheter to the hub outlet connector fitting when the distal tip of the catheter is sited at the desired internal body location; and,
  (e) connecting the proximal end of the subcutaneous catheter to the hub outlet connector fitting.

In a specific embodiment of the present invention, the tissue ingrowth cuff assembly comprises a single, unibody component comprised of a tubular portion permanently affixed to a skirt or flange portion. In alternative embodiments, the epidermal tissue ingrowth cuff assembly of the present invention may comprise a multiple-piece design, or a composite cuff in which the tube and skirt elements are separate cuff components. The multiple-cuff components of the composite design are brought together under the skin during placement of the device in the patient. As will be further described hereinafter, the composite cuff assemblies allow the user/physician to adjust the cuff assembly to suit the specific physiological requirements of the patient being treated in ways that cannot be achieved with any current CVC designs, and which are nowhere described or suggested by the current literature in this field.

In a preferred embodiment, the subcutaneous catheter is made detachable from the transcutaneous hub assembly. As will be recognized by those skilled in the art, this modular apparatus approach allows the catheter to be positioned within the patient using conventional chemotherapy port placement techniques. Chemotherapy ports are a conventional type of subcutaneous CVC that do not use tissue ingrowth cuffs. With a chemotherapy port, the catheter tip is positioned in the SVC/RA junction, and excess catheter length at the proximal end is available for trimming outside of the patient prior to assembling the catheter to the rest of the device. The detachable catheter feature as incorporated into the present invention offers another benefit in that, if problems occur with the catheter after it has been placed, the catheter can be replaced without compromising the adjustable tissue ingrowth cuff according to this invention.

Additionally, in all embodiments of the present invention, an extension tube component, denoted by reference numeral 112 in FIG. 1 (and by comparable numbers in other Figures), of the conduit assembly can be designed so that it can be repaired if breakage occurs through fatigue or abuse. The damaged extension tube 112 can be cut off adjacent to the rest of the conduit assembly (denoted generally by reference numeral 110 in FIG. 1 and by comparable numbers in other Figures) and a properly sized barbed fitting, with a new extension tube assembly, can then be inserted into the stump. This repair will allow the device to continue to function on at least a temporary basis until a more permanent solution can be implemented, such as replacing the device. It should be clear to those skilled in the art that the modular nature of the preferred embodiments of the present invention lend themselves well to both temporary and permanent repairs of the device.

All embodiments of the present invention also benefit from the addition of a component surface treatment to minimize or prevent the formation of thrombus or fibrin on the internal device surfaces. One such treatment is offered by Carmeda Corporation of San Antonio, Tex., in which heparin molecules are attached to a surface via the company's proprietary processes.

All embodiments of the present invention also benefit from the addition of a component surface treatment to minimize the ability of micro-organisms to live on the surface, and/or to reduce formation of biofilm. One such technique utilizes a locking fluid stored in the lumens of the device when not in use which inhibit biofilm formation. "Locking" refers to the practice of maintaining a column of anticoagulating liquid (i.e., heparinized saline) within the catheter lumen when the catheter is not being used. This prevents the catheter lumen from filling with blood and becoming clotted off. The liquid is injected to fill the lumen and the Halky Roberts clamp is closed to trap it in place. A company called Biolink, of Norwell, Mass., a manufacturer of subcutaneous dialysis ports requiring needles for access through the skin, offers such a locking fluid.

Also, all embodiments of the present invention may incorporate an additional conventional cuff on the catheter shaft designed to reside in the subcutaneous tunnel as an added precaution to infection or inadvertent catheter pull out.

For all embodiments of the present invention, the cuff materials may be treated with substances that further promote tissue ingrowth or vascularization. It is believed, for example, that biotechnology exists, or will soon emerge, that will enable clinicians to harvest specific cells, proteins, tissue matrixes, or other biomaterials, possibly from the specific patient in which the device of the present invention is to be placed, that could be used to prepare the cuff in such a way to accelerate tissue ingrowth, or strengthen the final bond between the skin and the cuff, or provide a more effective seal between the skin and cuff which would further decrease the ability of microbes to enter the patient at this location, or any other advantage which would enhance the performance of the novel invention described in this application. It is further anticipated that the entire cuff material could be fabricated from such a biomaterial and still be within the scope of this invention. These technologies are adjunctive in nature to the novel invention of this application.

Furthermore, it is believed that in some clinical applications it may be beneficial to provide the catheter apparatus of the present invention with a strain relief mechanism. Such a clinical application occurs for example in peritoneal dialysis, where the device is preferably tunneled in the subcutaneous tissue of the patient's abdomen, where it is exposed to significantly more flexural stresses than CVCs preferably placed in the upper torso. One such strain relief mechanism is described in U.S. Pat. No. 5,662,616 (Bousquet), where a flexible bellows component is integrated into the cuff and catheter assembly. Embodiments of the present invention can also be made to incorporate a strain relief mechanism, either subcutaneously or transcutaneously, by those skilled in the art, and such embodiments are also considered to be within the scope of this application.

BRIEF DESCRIPTIONS OF THE DRAWINGS

FIG. 1 is a schematic side view of a complete cuff/conduit/catheter assembly according to a first embodiment of this invention.

Figure 2A:
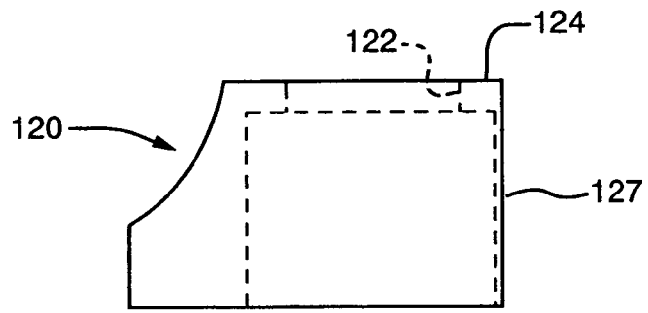
Figure 2B:
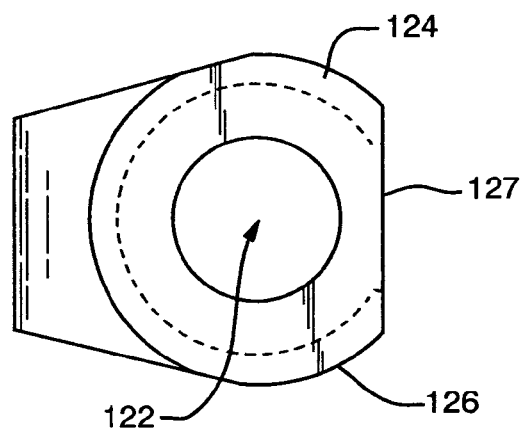
Figure 2C:
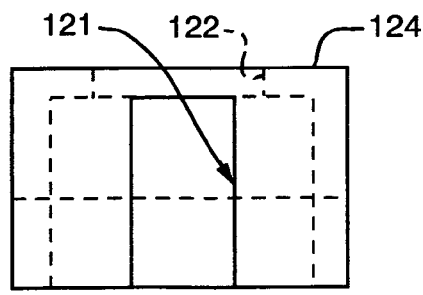

FIGS. 2A, 2B and 2C present various views of the base component or hub element according to the first embodiment of this invention.

Figure 3A:
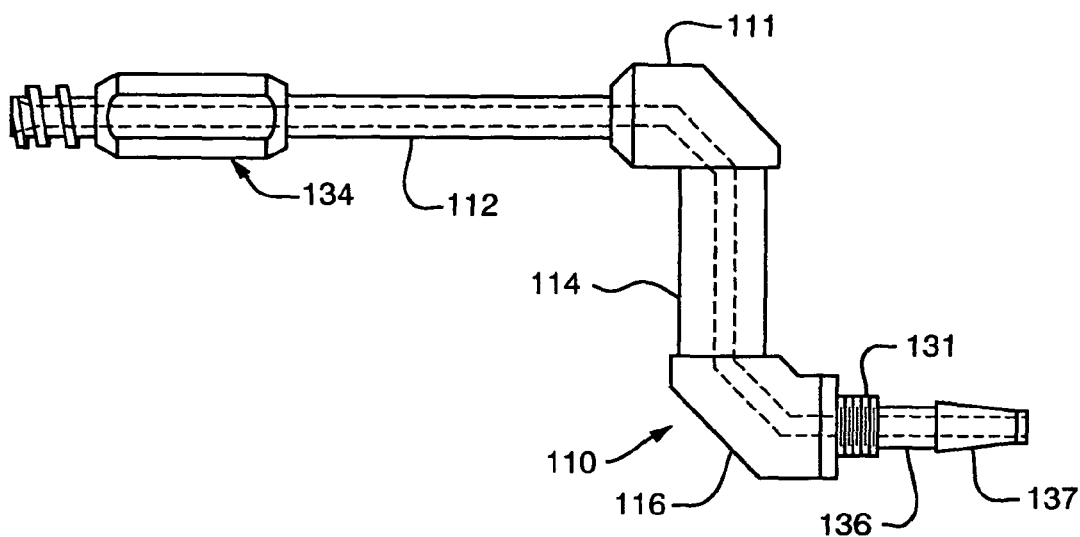
Figure 3B:
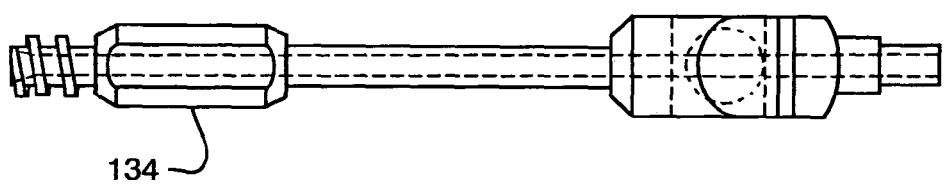
Figure 3C:
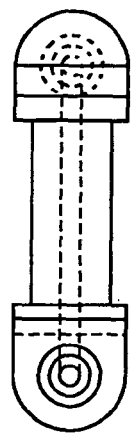

FIGS. 3A, 3B and 3C present various views of the conduit assembly component according to the first embodiment of this invention.

FIGS. 4A and 4B present two views of the catheter lock collar component according to the first embodiment of this invention.

FIGS. 5A and 5B present two views of the catheter shaft and catheter tip components according to the first embodiment of this invention.

FIGS. 6A and 6B present two views of the Dacron™ tube component according to the first embodiment of this invention.

FIGS. 7A and 7B present two views of the Dacron™ skirt or flange component according to the first embodiment of this invention.

Figure 8A:
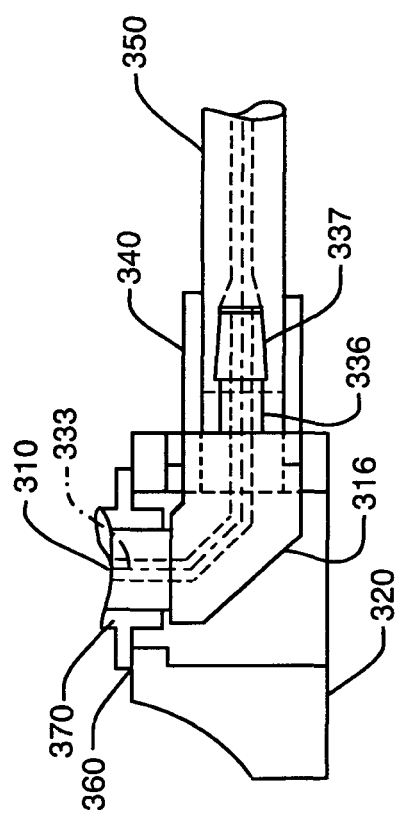
Figure 8B:
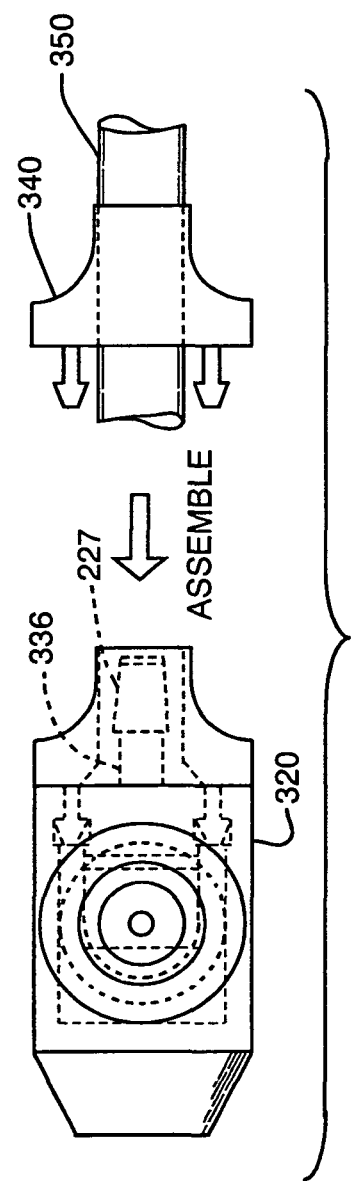

FIGS. 8A and 8B present two views of an alternative composite cuff system according to another embodiment of the present invention.

FIGS. 9A and 9B present two views of still another composite cuff system according to another embodiment of the present invention. FIG. 9C is a schematic sectional side view of a modified lock collar component 540.

Figure 10:
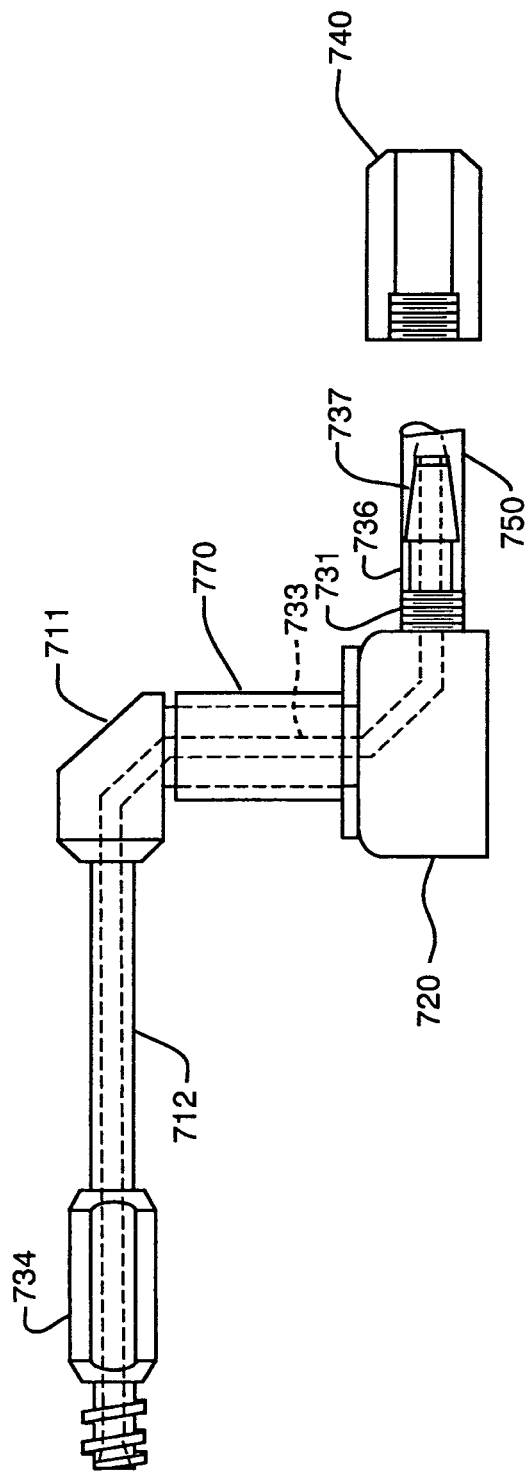

FIG. 10 presents a schematic side view of a unibody cuff embodiment according to the present invention.

DETAILED DESCRIPTION OF PREFERRED EMBODIMENTS

A first representative embodiment of a composite adjustable epidermal tissue ingrowth cuff assembly according to the present invention is illustrated in FIGS. 1-7. FIG. 1 is a schematic partial-sectional view of the complete cuff/conduit/catheter assembly 100 of the first embodiment of this invention. In FIG. 1, elements 120, 140, 160, and 170 are sectioned to show internal assembly details. As seen in FIG. 1, cuff/conduit/catheter assemblies according to this embodiment of the invention comprise in combination a cuff assembly, a conduit assembly, and a catheter portion, each comprising several cooperating elements as described below. A cuff base or hub component 120, shown in FIGS. 1 and 2 as a generally cylindrical shell or housing member having at least one and preferably two substantially flat external faces, or wall portions each having a substantially flat face thereon, is designed to be placed subcutaneously in a patient. The flat, generally circular end face 124 of base component 120 comprises an epidermal face which is generally closest to the skin surface following implantation of the hub assembly. Face 124 contains a circular hole 122 or epidermal face inlet substantially coaxial with generally circular end face 124 (better seen in FIG. 2B) sized to receive a short section of a hollow cylindrical tube 170 fashioned from an inert material known to be compatible with the epidermis. One familiar such material for the tube 170 is Dacron™. A substantially flat washer-like skirt or flange component 160, preferably fashioned from the same material as tube 170, namely Dacron™, is bonded to the epidermal face 124 of base 120 and includes a circular hole 162 coaxial with hole 122, hole 162 being sized and adapted securely to receive the tube. When the device is assembled, tube 170 extends from the hub interior region 125 of base 120, through holes 122 and 162, which are in coaxial alignment, to a location external of base 120. When the assembly is implanted in the patient, the external portion 172 of tube 170 (i.e., the portion that extends beyond skirt 160) will traverse the dermal layer and a portion will be located externally of the patient. The section of the tube 170 traversing the dermal layer is in intimate contact with it (i.e., slightly compressed by the dermal layer). The upper surface of the skirt 160 is in intimate contact with the undersurface of the dermal layer. The upper surface of the skirt 160 in combination with the outer surface of the tube portion 172 forms a composite, substantially continuous porous tissue ingrowth surface extending from a region surrounding hole 162 along the upper surface of skirt 160, along the outer surface of tube portion 172, to a location that is external of the patient (when the assembly is implanted in the patient). The outside diameter (OD) of the tube 170 may be generally between about ⅛ inch to ½ inch. The OD of the skirt 160 may be generally between about ¼ inch and 3 inches.

A conduit assembly 110 functions in cooperation with the cuff base assembly as described above. The conduit assembly 110 is shown having an external right-angle section 111 (which may include an extension tube section 112), a tube section 114 which passes through the interior of tube 170, a right-angle base component section 116 which passes through a passageway through the hub interior 125 of base 120, and hub outlet connector fitting 136 which passes through a hub outlet slot 121 (see FIG. 2C) in a flat portion 127 of the generally cylindrical side wall 126 of base 120. External section 111 of conduit assembly 110, or extension tube section 112, may be connected to a luer assembly 134 as shown in FIG. 1.

The generally cylindrical side wall 126 of base or hub component 120 includes a substantially flat face portion 127 which is slotted (see FIG. 2C) to accommodate the hub outlet connector fitting 136 seen in FIG. 1 projecting from the flat face portion 127 of side wall 126. Hub outlet connector fitting 136 includes an externally threaded section 131 adjacent to where it projects from face 127 and a barbed catheter connection fitting 137 at the other end. The proximal end of a catheter shaft 150, shown having a distal tip section 151, optionally with multiple side holes, is fitted over the barbed connection fitting 137 and secured in place with an internally threaded catheter lock collar 140 designed to mate with the externally threaded section 131 of connector fitting 136. The tunneled central (subcutaneous) catheter 150 as shown in FIG. 1 is a single-lumen catheter with a soft, atraumatic distal tip 151 shown having multiple side holes. The catheter tip 151 has features different from the rest of the catheter shaft 150, and thus should not be trimmed off. The catheter shaft 150 exits the patient's vasculature at a venotomy in the internal jugular vein. The shaft 150 proceeds through a tunnel under the patient's skin until it terminates at external thread section 131 of the conduit assembly 110. Outside of the patient, the conduit assembly may be connected to a luer assembly 134 by means of extension tube 112 as shown in FIG. 1. Conduit tube or channel 133 is shown in FIG. 1 extending through luer assembly 134, through extension tube 112, through the right-angle section 111 of conduit assembly 110, through tube section 114 of conduit assembly 110, through right-angle base section 116 of conduit assembly 110, through the flat wall section 127 of base component 120, through the catheter fitting connection 136 of conduit assembly 110, and finally through catheter shaft 150 to the catheter tip 151. These component elements of the embodiment of FIG. 1, and the associated methods for device placement in the body of a patient, for use, and for removal, are discussed in further detail below.

The soft tip 151 of the single lumen catheter shaft 150 can be positioned in the SVC/RA junction as follows. First, an entry needle is inserted into the internal jugular vein to gain access. A wire is then threaded through the needle deep into the vena cava. The needle is then removed over the wire and discarded. A peelable sheath/dilator assembly is then inserted over the wire into the vena cava. Next, a suitable position on the patient's torso for the cuff assembly is selected. A pocket incision of 2-3 cm. is made at that location in a direction perpendicular to that of the final intended path of the catheter through the tunnel. The tip 151 of the soft polymeric catheter shaft 150 is connected to a barbed end of a tunneler device. The sharp tip of the tunneler is then inserted under the skin at the pocket incision and pushed forward towards the sheath. Once the tunneler tip reaches the sheath, a small nick is made, if necessary, to allow the tunneler tip to exit the skin at the sheath location. Now the tunneler can be pulled forward, dragging the catheter shaft 150 behind it and positioning the catheter shaft 150 within the freshly created tunnel. Next the tunneler is removed from the catheter tip 151 and discarded, then the dilator is removed from the sheath and discarded, and the catheter shaft 150 is inserted through the sheath deep into the vena cava. The sheath is then peeled off the catheter and discarded. The catheter shaft 150 is further advanced and adjusted to ensure it is not kinked and that the tip 151 is in the desired position within the SVC/RA junction. The excess proximal catheter length is clamped outside of the 2-3 cm. pocket incision with a hemostat immediately proximal of the location where the catheter shaft 150 will be trimmed to length. The catheter shaft 150 is then retracted several centimeters from the patient and allowed to protrude from the 2-3 cm. pocket incision site with the clamp in place to prevent blood from escaping or air from entering the catheter shaft 150.

In the embodiment of FIG. 1, the cuff and conduit assemblies are then positioned as follows. A coring scalpel is used to create a small circular hole in the patient's epidermis adjacent to the 2-3 cm. pocket incision from which the excess catheter shaft 150 length now protrudes. A subcutaneous pocket connecting the incision with the circular hole is formed using blunt dissection. The base component 120 of the hub assembly, including the Dacron™ skirt component 160 of the epidermal tissue ingrowth cuff, is slid into the subcutaneous pocket. The base 120 provides the rigidity to ensure that the cuff skirt 160 remains flush, flat, and in intimate contact with the underside layer of the epidermis. The slot 121 in the base 120 is aligned parallel to the 2-3 cm. incision. Next, the conduit assembly 110, incorporating the Dacron™ tube component 170 of the final assembly (which tube is hermetically sealed to the exterior surface of the tube section 114 of conduit assembly 110), is inserted from the outside of the epidermis through both the circular hole in the skin and on through circular hole 122 in the base component 120 so that the barbed catheter connection fitting 137 is aligned within the base slot 121. The outside diameter of Dacron™ tube 170 and the inside diameter of the hole 162 in Dacron™ skirt 160 are sized to have an interference fit between them to insure circumferential contact. The conduit assembly 110 can now be adjusted in vertical height (or axially relative to base component 120 and tube 170 by spatially adjusting these components relative to one another) during the implantation procedure so that the composite, substantially continuous porous tissue ingrowth surface, i.e., the surface formed by the combination of the ingrowth surface of skirt component 160 and the ingrowth surface along just the transcutaneous tube portion 172 of tube 170, is correspondingly enlarged or reduced in size (surface area), in order that both the extension tube 112 level is close to the skin surface and the barbed catheter connection fitting 137 is exactly or nearly coincident with the axis of the subcutaneous tunnel.

Next, the catheter lock collar 140 is threaded over the proximal end of the catheter shaft 150. The catheter shaft 150 is trimmed to the appropriate length, as marked previously by the hemostat, and pushed over the barbed end 137 of the catheter connection fitting 136, which is both visible and accessible to the physician through the 2-3 cm. pocket incision. The lock collar 140 is then threaded onto the matching catheter connection fitting external threads 131 to secure and seal the catheter shaft 150 to the catheter connection fitting 136. The lock collar 140 may be further tightened to better secure the conduit assembly 110 to the base 120 at slot 121 such that the tube 170 is substantially perpendicularly aligned within base 120 and through the hole 162 in skirt 160 with no freedom to rotate or translate in the vertical (axial relative to tube 170) direction. Next, the 2-3 cm. incision is closed with sutures, and the extension tube 112 is secured to the patient's skin with an anchoring device (not shown). The anchoring device, such one manufactured by Venetec International Corporation of San Diego, Calif., described in U.S. Pat. No. 6,117,163, which patent is incorporated herein by reference, is needed for at least one week after implantation of the cuff assembly to allow time for the tissue to grow into the assembled composite cuff/conduit/catheter assembly without disruption, but still allow the luer fitting 134 to be manipulated during treatment while the tissue ingrowth is occurring.

As will be clear to those skilled in the art, the above description of apparatus and methods could equally apply to multiple lumen catheters with special tips, such as a dual lumen hemodialysis catheter in which the lumen exits are typically staggered along the length of the shaft by several centimeters, such as the configuration described by Mahurkar in U.S. Pat. No. 4,808,155, which patent is incorporated herein by reference. Another example would be the inclusion of a valve at the indwelling end of the catheter, such as that described by Groshong in U.S. Pat. No. 4,327,722, which patent is incorporated herein by reference.

Removal of the cuff assembly of this invention is also relatively simple and can be accomplished in several ways. In one preferred embodiment, the physician re-establishes the 2-3 cm. pocket incision, clamps the catheter shaft 150 closed with a hemostat distal of the catheter connection fitting 136, then cuts through the catheter shaft 150 proximal of the clamp. The catheter shaft 150 can now be removed from the patient. Next, a cut through the conduit assembly 110 and Dacron™ tube 170 immediately above the skin is made, and the upper part of the conduit assembly 110 with the attached extension tube 112 and with the luer assembly 134 is discarded. Blunt dissection is used to separate the epidermis from the Dacron™ or other cuff material 160 and 170 in the pocket and through the epidermis. The base 120 and remaining lower portion of the conduit assembly 110 are then removed from the pocket incision. The incision is then stitched and the annular hole through the epidermis is cleaned and bandaged. It will be clear to those skilled in this art, however, that other sequences of steps can successfully be employed to remove the devices of the present invention.

FIGS. 2A, 2B, and 2C are views showing structural details of the cuff base component 120 shown in FIG. 1. FIG. 2A is a schematic side view which isolates the cuff base component 120 shown from the same perspective as seen in FIG. 1. FIG. 2B is a top view of the cuff base component 120 as shown in FIG. 2A. FIG. 2B better shows the circular hole 122 running through the top flat face 124 of base 120, hole 122 being substantially coaxial relative to the generally cylindrical portion of the side wall 126 of base 120. In a preferred embodiment, the internal diameter of hole 122 in top face 124 should be greater than, for example about 1/16 inch greater than, the internal diameter of hole 162 through skirt 160. FIG. 2B also shows the substantially flat, slotted portion 127 of side wall 126 of base 120.

FIG. 2C is a right side view of the cuff base component 120 as shown in FIG. 2A. FIG. 2C better shows the base slot 121 of cuff base component 120 which accommodates limited axial adjustability of the catheter connection fitting 136 prior to tightening lock collar 140.

The cuff base component 120 may be fabricated out of any generally inert, body-compatible material having sufficient structural strength, for example titanium, polyurethane or polysulfone. The specific geometry of the cuff base component 120 need not be limited to the generally cylindrical structure as shown in FIGS. 1 and 2, but rather can be optimized for patient comfort and to minimize wasted internal body space. The bearing surfaces of base slot 121 can optionally be reinforced, for example using titanium clips, to ensure rigidity of the fully assembled apparatus.

FIGS. 3A, 3B and 3C are views showing structural details of the conduit assembly 110 shown in FIG. 1 prior to the hermetic sealing of the tube 170 to tube 114, which occurs during the manufacture of the device. FIG. 3A is a schematic side view which isolates the conduit assembly 110 as shown from the same perspective as seen in FIG. 1. FIG. 3B is a top view of the conduit assembly 110 as shown in FIG. 3A. FIG. 3B better shows how the right-angle external section 111 connects with tube section 114 of conduit assembly 110. FIG. 3C is a right side view of the conduit assembly 110 as shown in FIG. 3A. FIG. 3C better shows how right-angle external section 111 and right-angle base section 116 of the conduit assembly join respectively to extension tube 112 and to catheter connection fitting 136.

Conduit assembly 110 may be manufactured as an assembly of several component elements provided that all joints between component elements are hermetically sealed. The component elements comprising conduit assembly 110 may be fabricated out of any generally inert, body-compatible material having sufficient structural strength, for example titanium, polyurethane or polysulfone. It is conventional to include a Halkey-Robert clamp (not shown) along extension tube 112. The overall height of conduit assembly 110 (measured axially relative to tube 170 and conduit tube section 114) can be reduced by making the 45° angle sections 111 and 116 shorter or by shortening tube section 114 and Dacron™ tube 170 (see FIG. 1). Connections from conduit assembly 110 to ancillary devices (e.g., syringe, blood line, etc.) can be made via a standard female luer fitting 134.

FIGS. 4A and 4B are views showing structural details of the lock collar element 140 shown in FIG. 1. FIG. 4A is a schematic side view which isolates the lock collar element 140 as shown from the same perspective as seen in FIG. 1. FIG. 4B is a right-side end view of lock collar element 140 as shown in FIG. 4A. FIGS. 4A and 4B better show the internal threads at the non-tapered proximal end of lock collar 140, those threads being designed to mate with the external threads 131 at the proximal end of the catheter connection fitting section 136 of the conduit assembly 110 (see FIG. 1).

The inside diameter of the center opening of lock collar 140 is preferably slightly smaller than the outside diameter of the catheter shaft 150 which is threaded through the inside of lock collar 140 (see FIG. 1) to provide a compression fit when the components are fully assembled. Lock collar 140 may be fabricated out of any generally inert, body-compatible material having sufficient structural strength, for example titanium, polyurethane, polysulfone or delrin (acetal). Although shown in FIGS. 1 and 4A, 4B as a generally cylindrical element partially tapered at one end, it should be understood that the exterior surface of lock collar 140 may be contoured to compliment the geometry of base component 120 to increase patient comfort.

FIGS. 5A and 5B are views showing structural details of the catheter shaft 150 and catheter tip portion 151 shown in FIG. 1. FIG. 5A is a schematic side view which isolates the catheter shaft 150 as shown from the same perspective as seen in FIG. 1. FIG. 5B is a right-side end view of catheter shaft 150, particularly tip portion 151, as shown in FIG. 5A. As seen in FIG. 5A, the tip portion 151 of catheter shaft 150 preferably includes multiple side holes 153 and a tapered distal end 155. Accordingly, in this embodiment it is important that the tip portion of catheter shaft 150 not be trimmed off during the procedure for positioning the device.

The catheter shaft 150 may be fabricated from any generally inert, body-compatible elastomeric material, for example polyurethane or silicone. Unit of length markings, for example in centimeters, may be provided along the length of the catheter starting at the tip. Catheter surfaces may be coated with materials to provide special therapeutic properties, for example with anti-thrombus or anti-microbial materials. In addition to the epidermal tissue ingrowth cuff assemblies of the present invention, it may also be desirable to provide the catheter shaft with a secondary cuff, made for example of Dacron™, somewhere along its length for added resistance to being unintentionally pulled out or moved. In a two-catheter hemodialysis system, the proximal end of each catheter might include a differently colored indicator mark, such as red and blue, to identify which is a venous and which is an arterial catheter. Proximal markings also can be used in multi-lumen catheters to allow identification of different lumen sizes or end hole geometries during connection after the tip is in the body.

FIGS. 6A and 6B are views showing structural details of the preferably Dacron™ tube component 170 of the conduit assembly 110 shown in FIG. 1. FIG. 6A is a schematic side view which isolates the tube 170 as shown from the same perspective as seen in FIG. 1. FIG. 6B is a top view of tube 170 as shown in FIG. 6A. FIGS. 6A and 6B show the cylindrical geometry of tube 170 which, as seen in FIG. 1, is sized to receive and be hermetically sealed around tube section 114 of conduit assembly 110. In a preferred embodiment, the pore size of the Dacron™ of tube 170 ranges from about 20 to 2000 microns. The thickness of the cylindrical walls of tube 114 must be adequate to structurally support the associated conduit assembly components, for example about 3/32 inch to 3/16 inch nominal thickness will typically suffice.

FIGS. 7A and 7B are views showing structural details of the preferably Dacron™ skirt or flange element 160 which is adhered to the external surface of flat end face 124 of base component 120 as shown in FIG. 1. FIG. 7A is a schematic side view which isolates skirt 160 as shown from the same perspective as seen in FIG. 1. FIG. 7B is a top view of skirt 160 as shown in FIG. 7A. FIG. 7B better shows the generally circular geometry of skirt 160 except for flat side portion 165 which, on bonding skirt 160 to face 124, is oriented to align with the flat portion 127 of side wall 126 of base component 120. As previously noted, the internal diameter of hole 162 in skirt 160 is preferably sized relative to the outside diameter of tube 170 so as to obtain an interference fit between them to insure complete circumferential contact. For example, the ID of hole 162 might be about 1/16 inch smaller than the OD of tube 170.

FIGS. 8A and 8B illustrate an alternative embodiment of a composite adjustable epidermal tissue ingrowth cuff system according to the present invention. FIG. 8A is a schematic sectional side view of the alternative cuff system. FIG. 8B is a top view of the system as shown in FIG. 8A. The embodiment of FIGS. 8A and 8B is generally quite similar to the composite adjustable cuff embodiment of FIGS. 1-7, the principal difference being that in the embodiment of FIGS. 8A and 8B the barbed catheter connection fitting 136 of FIG. 1 does not include external threads 131 (see FIG. 3A). Instead, an alternative structure and method are utilized to securely connect catheter shaft 350 in FIGS. 8A and 8B to the catheter connection fitting 336 at the distal end of conduit assembly 310.

The procedure for utilizing the apparatus of FIGS. 8A and 8B is the same as described in previous sections except that assembly of this composite cuff is accomplished by snapping the lock collar 340 (which is modified from the lock collar 140 of FIGS. 1 and 4 by the elimination of both the tapered distal end and the internal threads at the proximal end) into place inside base component 320 and about the distal end of base component section 316 of conduit assembly 310, as shown in FIGS. 8A and 8B. For this embodiment of the present invention, it is preferred that base component 320 and lock collar 340 have, respectively, matching male and female ergonomic contours, as seen in FIG. 8B, to facilitate one-hand assembly.

Although the composite structure of FIGS. 8A and 8B does not have a screw-tight lock collar, as in FIG. 1, to prevent vertical (i.e., axial relative to the axis of base component 320 and tube section 370) movement of the distal end of the conduit assembly in the slot of base component 320 (corresponding to slot 121 in FIG. 2C), the critical dimensions of this structure can be closely toleranced in order to achieve a tight fit which minimizes such vertical movement.

FIGS. 9A, 9B and 9C illustrate still another alternative embodiment of a composite adjustable epidermal tissue ingrowth cuff system according to the present invention. FIG. 9A is a schematic sectional side view of a modified, mostly solid base component 520 having a Dacron™ skirt element 560 adhered to a substantially flat face of base component 520 corresponding generally to face 124 of base component 120 in FIG. 1. FIG. 9B is a schematic partial sectional side view of a modified conduit assembly 510 comprising an extension tube section 512 connected to a luer assembly 534, and a Dacron™ tube section 570 defining conduit channel/tube 533. FIG. 9C is a schematic sectional side view of a modified lock collar component 540.

Assembly of this composite cuff system is accomplished by first pushing the free end of conduit channel/tube 533 over the conduit barb fitting 529 which is incorporated into base component 520. Conduit tube 533 can be trimmed to the proper length by the user prior to assembly. At least limited rotation of conduit assembly 510 relative to base component 520 is possible in single lumen designs, but can be minimized either by specifying and machining components to tight interference tolerances, or by using non-circular geometries, or both.

Conduit barbed fitting 529 and catheter connection barbed fitting 537 projecting from base component 520 can comprise a single metal foundation assembly over which base 520 is molded. The barbed fittings 529 and 537 may comprise either a single barb (fitting 537 for example) or multiple barbs (fitting 529 for example). Also barbed fittings 529 and 537 may be fabricated out of either metal or plastic. Lock collar 540 is sized to provide an interference fit between the outside diameter of the catheter shaft 550 and the barbed fitting 537.

FIG. 10 illustrates an alternative embodiment of an adjustable cuff system according to the present invention comprising a unibody cuff design as an alternative to the various composite cuff systems described above. As seen in FIG. 10, the unibody cuff design of this embodiment of this invention comprises a base component portion 720 having an integrated cuff or skirt element 760 along one flat face and also having a barbed catheter connection fitting portion 736 projecting from a sidewall of base component portion 720, a tube portion 770 projecting from the flat face/skirt 760 of base component portion 720, and a conduit portion comprising the right-angle conduit member 711 connected at one end to the end of tube portion 770 and connected at the other end to an extension tube portion 712 which is connected at one end to luer assembly 734.

Conduit tube or channel 733 is seen to run completely through the interior of this unibody apparatus from the luer assembly at the proximal end to the tip of the barbed element 737 of the connection fitting portion 736. As seen in FIG. 10, the proximal end of catheter connection fitting portion 736 includes external threads 731 designed to mate with internal threads at the proximal end of catheter lock collar 740, which is used to secure catheter shaft 750 to catheter connection fitting portion 736. In this configuration, the tube portion 770 and conduit portions 711 and 712 are incorporated into base 720 for stability.

The unibody cuff design as illustrated in FIG. 10 has some advantages (such as ease of manufacture, lower cost, simpler to place) and also some disadvantages relative to the composite cuff designs as described above. In the unibody cuff embodiment, the luer assembly 734 must pass through the skin incision in order to accomplish placement of the base and cuff. This may be of little concern if these unibody assemblies are not substantially bulkier than the cuff assembly, as may be the case in a single lumen catheter device. Dual lumen and triple lumen devices, which incorporate multiple luers 734 and tubes 712, as well as multiple Halky Roberts clamps (not shown), will be substantially bulkier than the cuff assembly by itself, and these devices therefore benefit significantly from the composite cuff designs described earlier. The composite cuff designs as described above have several other advantages over the unibody cuff design including but not limited to:

1. The composite devices can be assembled at the skin and adjusted in a manner that ensures all components are positioned ideally relative to the skin. The bulky hub and luer fittings do not have to pass through the skin, as is required with the unibody design, thereby enabling the cuff incision to be minimized and undisturbed prior to contact with the tissue ingrowth cuff material.
2. The proper component positions can be readily confirmed visually and accessed manually for adjustment via the incision with the composite cuff designs.
3. The length of the component traversing the epidermis, and correspondingly the size (surface area) of the composite, substantially continuous porous tissue ingrowth surface as herein defined, can be readily adjusted during an implantation procedure to conform to the patient's specific physiology with the composite cuff designs.

These advantages simplify and accelerate the proper placement procedure, which is of great significance and value to the physician. Proper placement in turn maximizes the probability that the composite cuff will promote epidermal tissue ingrowth as intended, which is also of great significance and value to both the physician and the patient.

The present invention also has other important advantages and distinctions over related types of prior art medical devices. Devices according to the present invention might be classified as belonging to a subset of body access devices. This subset would be access devices which are transcutaneous and which require assembly at the time of placement. Physicians are willing to perform assembly steps during placement if additional clinical advantages can be realized. These advantages include being able to adjust the device size and/or geometry to the patient's physiology, for example by adjusting the length of the transcutaneous tube portion and, correspondingly, the size (surface area) of the composite, substantially continuous porous tissue ingrowth surface, for purposes of comfort or enhancing device performance or device longevity.

The devices of the present invention are unique compared with related prior art devices in several respects. Only the composite cuff designs of this invention have the following combination of attributes:

(a) 2-piece flanged cuff design designed to promote epidermal tissue ingrowth at the skin exit site;
(b) Cuff design which is adjustable in height to allow for different skin thicknesses;
(c) Cuff design which allows the use of a flanged cuff and precise adjustability of the catheter tip location;
(d) All assembled components reside subcutaneously to eliminate paths for microbial migration on the device's exterior surfaces; and
(e) The entire device, once assembled, is locked together with one or no degrees of freedom to move (x, y, z planes, or rotationally) which provides the stability needed to allow tissue ingrowth to occur within 1-2 weeks.

Prior art CVC devices are either subcutaneous or transcutaneous. An example of a subcutaneous device is that described in U.S. Pat. No. 4,673,394 (Fenton et al.) entitled "Implantable Treatment Reservoir," which patent is incorporated herein by reference. An example of a transcutaneous device is that described in U.S. Pat. No. 4,808,155 (Mahurkar) entitled "Simple Dual Lumen Catheter," which patent is also incorporated herein by reference. The tissue ingrowth cuff assemblies of the present invention differ from the subcutaneous prior art devices because the devices of this invention use a transcutaneous design.

Prior art CVC devices are either of single-component construction (including the catheter shaft), thus requiring no assembly during placement, or else have multiple components requiring complex assembly during placement in the body. Examples of single-component CVC devices are found in U.S. Pat. No. 4,808,155 (Mahurkar) entitled "Simple Dual Lumen Catheter," and U.S. Pat. No. 5,718,678 (Fleming) entitled "Multilumen Coaxial Catheter and Method of Making the Same," which patent is incorporated herein by reference. The adjustable tissue ingrowth cuff systems of the present invention differ from all single-component prior art devices because they are all designed to have at least a separate catheter component which can be adjusted relative to the cuff component or components during placement in the body.

Within the field of multiple-component, transcutaneous medical devices, the prior art devices have components which fall into either one of two types. In the first type, the multiple components are assembled and remain at least partly outside the body. An example is U.S. Pat. No. 5,776,111 (Tessio) entitled "Multiple Catheter Assembly," which patent is incorporated herein by reference. The adjustable cuff systems of the present invention differ from this prior art in that substantially all of the assembled components of the various embodiments of the present invention reside entirely within the body.

In the second type of multiple-component, transcutaneous medical devices, components are assembled and placed completely inside the body. This prior art differs from the present invention in that none of the assembled components residing within the body in these prior art devices are designed to be positioned immediately adjacent to the skin exit site for the purpose of promoting skin ingrowth. Having all critical assembly surfaces occur inside the patient is a unique and important feature of the present invention. If the adjustable tissue ingrowth cuff of this invention functions as intended, the cuff's exterior surface is fully protected by the skin from microbial colonization. With the present invention, all device exterior surfaces outside of the patient are hermetically sealed during the manufacturing process so that no path for infection exists to allow microbial migration into the patient.

Although the focus of this invention has been on establishing a permanent, or at least long-term, port from outside the body, through the epidermis, and into the body, typically via a blood vessel, in order to reach a desired interior body location, for the purpose of delivering fluids to, or withdrawing fluids from, the desired interior body location, it will be understood to those skilled in this art that the adjustable epidermal tissue ingrowth cuffs of the present invention can be used to create more or less permanent body ports for other therapeutic purposes. Thus, it is envisioned that an epidermal tissue ingrowth cuff according to the present invention could be utilized to create a long-term body port connected to an internally-placed catheter shaft which could be used to thread a medical instrument to a desired interior body location for continuous or periodic treatment and/or monitoring.

In a related alternative embodiment, an adjustable epidermal tissue ingrowth cuff according to the present invention could be utilized to create a long-term body port connected to an internally-placed catheter shaft for continuously or periodically delivering a heat exchange fluid at a temperature above or below normal body temperature to a desired interior body location. For example, U.S. Pat. No. 5,624,392 (Saab) and U.S. Pat. No. 5,902,268 (Saab), which patents are incorporated herein by reference, describe heat transfer catheter apparatuses and methods of making and using such apparatuses, which devices and techniques may be advantageously utilized in conjunction with the adjustable epidermal tissue ingrowth cuffs of the present invention.

It will be apparent to those skilled in the art that other changes and modifications may be made in the above-described apparatus for adjustable epidermal tissue ingrowth cuffs and methods for using that apparatus without departing from the scope of the invention herein, and it is intended that all matter contained in the above description shall be interpreted in an illustrative and not a limiting sense.

Having described my invention, what I claim is:

1. A medical apparatus for establishing a long-term body access channel sealed along its length and extending from a proximal location outside the skin surface, through the epidermis, and into a living body, said apparatus comprising:
   (a) a hub component designed to be implanted subcutaneously, said hub component comprising a hub top side with a hub top side upper face that faces the skin surface when the hub component is implanted and a hub top side lower face that faces away from the skin surface, a hub sidewall extending from the hub top side to a location beyond the hub top side lower face in a direction away from the skin surface, and a hub passageway extending between a passageway inlet at the hub top side upper face and a passageway outlet at the hub sidewall, and also wherein a longitudinal axis of the hub passageway at the hub top side is oriented transversely relative to a longitudinal axis of the hub passageway at the hub sidewall;
   (b) a transcutaneous hub tube mated with the hub passageway when said hub component is implanted such that a proximal hub tube end extends above the skin surface, a transcutaneous hub tube portion extends between the skin surface and the hub passageway at least to the hub top side lower face, and the transcutaneous hub tube terminates before reaching the passageway outlet, and a transcutaneous conduit runs seriatim from outside the body, through the hub tube and said hub passageway, and into the body interior; and,
   (c) porous tissue ingrowth surfaces along the hub top side upper face and also along the outside of at least a section of the proximal hub tube end and the transcutaneous portion of the hub tube such that porous tissue ingrowth surface extends along the hub tube from above the skin surface at least to the hub top side lower face and terminates before reaching the passageway outlet.

2. An apparatus according to claim 1 further wherein said hub component and hub tube consist essentially of a material which is compatible with the epidermis.

3. An apparatus according to claim 1 wherein a distal end of the transcutaneous conduit is connected with the proximal end of an implanted subcutaneous conduit to extend the access channel to more remote regions of the body.

4. An apparatus according to claim 1 wherein said porous surfaces comprise surface pores ranging in size between about 20-2000 microns.

5. An apparatus according to claim 1 further wherein said porous tissue ingrowth surfaces consist essentially of polyester.

6. A medical apparatus for establishing a long-term body access channel sealed along its length and extending from a proximal location outside the skin surface, through the epidermis, and into a living body, said apparatus comprising:
   (a) a hub component designed to be implanted subcutaneously, said hub component comprising a hub top side with a hub top side upper face that faces the skin surface when the hub component is implanted and a hub top side lower face that faces away from the skin surface, a hub sidewall extending from the hub top side to a location beyond the hub top side lower face in a direction away from the skin surface, and a hub passageway extending between a passageway inlet at the hub top side upper face and a passageway outlet at the hub sidewall, and also wherein a longitudinal axis of the hub passageway at the hub top side is oriented transversely relative to a longitudinal axis of the hub passageway at the hub sidewall;
   (b) a transcutaneous hub tube mated with the hub passageway when said hub component is implanted such that a proximal hub tube end extends above the skin surface, a transcutaneous hub tube portion extends between the skin surface and the hub passageway at least to the hub top side lower face, the transcutaneous hub tube terminates before reaching the passageway outlet, and the passageway outlet abuts or comprises a collar element that extends from inside the hub passageway through the hub sidewall, and a transcutaneous conduit runs seriatim from outside the body, through the hub tube, the hub passageway and the collar element, and into the body interior; and,
   (c) porous tissue ingrowth surfaces along the hub top side upper face and also along the outside of at least a section of the proximal hub tube end and the transcutaneous portion of the hub tube such that porous tissue ingrowth surface extends along the hub tube from above the skin surface to below the hub top side lower face and terminates before reaching the passageway outlet.

7. A medical apparatus for establishing a long-term body access channel sealed along its length and extending from a proximal location outside the skin surface, through the epidermis, and into a living body where the channel or a transcutaneous conduit comprising the channel is or can be subcutaneously connected to the proximal end of an implanted subcutaneous catheter, said apparatus comprising:

(a) a hub component designed to be implanted subcutaneously, said hub component comprising a hub top side with a hub top side upper face that faces the skin surface when the hub component is implanted and a hub top side lower face that faces away from the skin surface, a hub sidewall extending from the hub top side to a location beyond the hub top side lower face in a direction away from the skin surface, and a hub passageway extending between a passageway inlet at the hub top side upper face and a passageway outlet at the hub sidewall, and also wherein a longitudinal axis of the hub passageway at the hub top side is oriented transversely relative to a longitudinal axis of the hub passageway at the hub sidewall;

(b) a transcutaneous hub tube mated with the hub passageway when said hub component is implanted such that a proximal hub tube end projects above the skin surface, a transcutaneous hub tube portion extends between the skin surface and the hub passageway at least to the hub top side lower face, the transcutaneous hub tube terminates before reaching the passageway outlet, and a transcutaneous conduit runs seriatim from outside the body, through the hub tube and hub passageway; and, (c) a hub connector fitting at the distal end of said transcutaneous conduit to provide a connection to the proximal end of an implanted subcutaneous catheter, wherein said hub connector fitting comprises a threaded collar that may be tightened to better secure the conduit to the hub component in graduated tightening increments at the juncture between the distal end of the transcutaneous conduit and the proximal end of the subcutaneous catheter; and (d) porous tissue ingrowth surfaces along the hub top side upper face and also along the outside of at least a section of the proximal hub tube end and the transcutaneous portion of the hub tube such that porous tissue ingrowth surface extends along the hub tube from above the skin surface to below the hub top side lower face and terminates before reaching the passageway outlet.

8. An apparatus according to claim 7 wherein the collar is sized to fit concentrically around a hub outlet connector, said collar having internal threads at its proximal end sized to engage and mate with external threads of the hub outlet connector, such that rotation of the collar tightens the connection between the hub component and the conduit in graduated tightening increments.

9. A medical apparatus for establishing a long-term body access channel sealed along its length and extending from a proximal location outside the skin surface, through the epidermis, and into a living body where the channel or a transcutaneous conduit comprising the channel is or can be subcutaneously connected to the proximal end of an implanted subcutaneous catheter, said apparatus comprising:

(a) a hub component designed to be implanted subcutaneously, said hub component comprising a hub top side with a hub top side upper face that faces the skin surface when the hub component is implanted and a hub top side lower face that faces away from the skin surface, a hub sidewall extending from the hub top side to a location beyond the hub top side lower face in a direction away from the skin surface, and a hub passageway extending between a passageway inlet at the hub top side upper face and a passageway outlet at the hub sidewall;

(b) a transcutaneous hub tube mated with the hub passageway when said hub component is implanted such that a proximal hub tube end projects above the skin surface, a transcutaneous hub tube portion extends between the skin surface and the hub passageway at least to the hub top side lower face, the transcutaneous hub tube terminates before reaching the passageway outlet, and a transcutaneous conduit runs seriatim from outside the body, along a first axis into the portion of the hub tube that is mated with the proximal end of the hub passageway, through said tube and hub passageway, and out of the distal end of said hub passageway along a second axis that is oriented transversely relative to the first axis;

(c) a fitting external to the hub passageway that maintains the hub tube in place relative to the hub component; and, (d) porous tissue ingrowth surfaces along the hub top side upper face and also along the outside of at least a section of the proximal hub tube end and the transcutaneous portion of the hub tube such that porous tissue ingrowth surface extends along the hub tube from above the skin surface at least to the hub top side lower face and terminates before reaching the passageway outlet.

10. A medical apparatus for establishing a long-term body access channel sealed along its length and extending from a proximal location outside the skin surface, through the epidermis, and into a living body where a transcutaneous conduit that runs through the channel is or can be subcutaneously connected to the proximal end of an implanted subcutaneous catheter, said apparatus comprising:

(a) a hub component designed to be implanted subcutaneously, said hub component comprising a hub top side with a substantially flat hub top side upper face that faces the skin surface when the hub component is implanted and a hub top side lower face that faces away from the skin surface, a hub sidewall extending from the hub top side to a location beyond the hub top side lower face in a direction away from the skin surface, and a hub passageway extending between a passageway inlet at the substantially flat hub top side upper face and a passageway outlet at the hub sidewall;

(b) a transcutaneous hub tube mated with the hub passageway when the hub component is implanted such that a proximal hub tube end projects above the skin surface, a transcutaneous hub tube portion extends between the skin surface and the hub passageway at least to the hub top side lower face, the transcutaneous hub tube terminates before reaching the passageway outlet, and a transcutaneous conduit runs seriatim from outside the body, through the hub tube and hub passageway;

(c) a fitting external to the hub passageway that securely fixes the hub tube in place relative to the hub component for the duration of the long-term use; and, (d) porous tissue ingrowth surfaces along the substantially flat hub top side upper face surrounding an entrance to the hub passageway and also along the outside of at least a section of the proximal hub tube end and the transcutaneous portion of the hub tube such that porous tissue ingrowth surface extends along the hub tube from above the skin surface to a location below the hub top side upper face and terminates before reaching the passageway outlet.

11. An apparatus according to claim 10 further wherein said hub tube and hub component consist essentially of a material which is compatible with the epidermis and promotes tissue ingrowth.

12. An apparatus according to claim 10 further wherein porous tissue ingrowth surface along the outside of said hub tube extends below the hub top side lower face.

13. A medical apparatus for establishing a long-term body access channel sealed along its length and extending from a proximal location outside the skin surface, through the epidermis, and into a living body where the channel is or can be subcutaneously connected to the proximal end of an implanted subcutaneous catheter, said apparatus comprising:
 (a) a hub component designed to be implanted subcutaneously, said hub component comprising a two-level hub top side with upper and recessed levels and also with a hub top side upper face that faces the skin surface when the hub component is implanted and a hub top side lower face that faces away from the skin surface, a hub sidewall extending from the hub top side in a direction away from the skin surface, a first hub connector fitting projecting outwardly from the recessed level of said hub top side and having a barbed end, and a hub passageway extending through the barbed end connector fitting and the hub to the hub sidewall;
 (b) a transcutaneous hub tube mated with the hub connector fitting when said hub component is implanted such that a proximal hub tube end projects above the skin surface, a transcutaneous hub tube portion extends between the skin surface and the recessed level of the hub top side, and a transcutaneous conduit runs seriatim from outside the body, through the epidermis, through said hub tube, and into the body interior, wherein the conduit section housed inside the hub tube is sized to engage the barbed end of the first hub connector fitting when the hub tube is mated with the hub connector fitting; and,
 (c) porous tissue ingrowth surfaces along at least the upper level of the hub top side upper face and also along the outside of at least a section of the proximal hub tube end and the transcutaneous portion of the hub tube such that porous tissue ingrowth surface extends along the hub tube from above the skin surface to the recessed level of the hub top side.

14. An apparatus according to claim 13 further comprising a second hub connector fitting projecting outwardly from the hub sidewall and having a barbed end.

15. An apparatus according to claim 14 further comprising an implanted subcutaneous catheter having a proximal end sized to engage the barbed end of the second hub connector fitting.

16. A medical port for establishing a body access channel that extends from a location outside the body, through the skin surface, and into a living body, wherein the port comprises: a hub component designed to be implanted subcutaneously such that there is a first hub face oriented generally toward the skin surface, the opposite side of the first hub face is a second hub face oriented generally away from the skin surface, and a hub side face extends from the second hub face in a direction away from the skin surface; a hub passageway connects the first hub face and the hub side face and a longitudinal axis of the hub passageway at the first hub face is oriented transversely relative to a longitudinal axis of the hub passageway at the hub side face; a conduit mated with the hub passageway when the hub component is implanted establishes a sealed channel that extends from outside the body, through the skin surface and into the hub passageway; and, there is a porous tissue ingrowth surface along the first hub face and also a porous tissue ingrowth surface along a portion of the outer surface of the conduit that begins in the hub passageway and extends between the second hub face and a location above the skin surface so as to establish a substantially continuous porous tissue ingrowth surface from the second hub face to above the skin surface.

17. A medical port according to claim 16 further wherein the porous tissue ingrowth surfaces along the outer surface of the conduit extends from below the second hub face to a location above the skin surface.

18. A medical port according to claim 16 further wherein the hub component consists essentially of a material that is biocompatible.

19. A medical port according to claim 16 wherein the porous tissue ingrowth surfaces comprise surface pores ranging in size between about 20-2,000 microns.

20. A medical port according to claim 16 further wherein the hub component and the conduit comprise an inert material.

21. A medical port according to claim 16 further wherein at least a surface of the medical port is treated to reduce the formation of thrombus.

22. A medical port according to claim 16 further wherein at least a surface of the medical port is treated to control microorganisms.

23. A medical apparatus for establishing a long term body access channel extending from a location outside the skin surface, through the epidermis, and into a living body, said apparatus comprising:
 (a) a subcutaneous member comprising an upper wall with a top face that faces the skin surface when the subcutaneous member is implanted and a bottom face that faces away from the skin surface, a sidewall that extends from the bottom face to a location beyond the bottom face, and a passageway through the subcutaneous member starting at the top face and extending to the sidewall wherein a longitudinal axis of the passageway at the top face is oriented transversely relative to a longitudinal axis of the passageway at the sidewall, and a top face porous tissue ingrowth surface at least along a portion of said top face adjacent the passageway;
 (b) a transcutaneous conduit mated with said passageway when the subcutaneous member is implanted such that a proximal end projects above the skin surface thereby establishing a transcutaneous access channel extending from outside the skin surface into the body interior region; and,
 (c) a conduit porous tissue ingrowth surface at least along a portion of the outer surface of the transcutaneous conduit that begins in the passageway and extends transcutaneously from beneath the top face of the upper wall, through the skin, to a point above the external skin surface when said subcutaneous member is implanted.

24. A medical apparatus according to claim 23 further wherein said subcutaneous member comprises a structure sized, shaped, and subcutaneously positioned to minimize movement of the porous tissue ingrowth surfaces while allowing the orientation of the conduit to be changed from a path generally parallel to the skin surface where the conduit is distal of the subcutaneous member to a path that intersects the skin surface when the conduit is proximal of the subcutaneous member.

25. A medical apparatus according to claim 24 wherein the structure includes a fitting proximal of the subcutaneous member that restricts movement of the mated transcutaneous conduit.

26. A medical apparatus according to claim 24 wherein the structure includes a fitting distal of the subcutaneous member that restricts movement of the mated transcutaneous conduit.

27. A medical apparatus according to claim 23 further wherein the porous tissue ingrowth surfaces along the outer surface of the transcutaneous conduit extends from beneath the bottom face of the upper wall to a point above the external skin surface.

28. A medical apparatus according to claim 23 further wherein said subcutaneous member consists essentially of a material that is compatible with living dermal tissue.

29. A medical apparatus according to claim 23 further wherein said subcutaneous member consists essentially of a material that is compatible with living non-dermal tissue.

30. A medical apparatus for establishing a long term body access channel extending from a location outside the skin surface, through the epidermis, and into a living body, said apparatus comprising:
  (a) a subcutaneous member comprising an upper wall with a top face that faces the skin surface when the subcutaneous member is implanted and a bottom face that faces away from the skin surface, a sidewall that extends from the bottom face to a location beyond the bottom face, and a passageway through the subcutaneous member starting at the top face and extending to the sidewall wherein a longitudinal axis of the passageway at the top face is oriented transversely relative to a longitudinal axis of the passageway at the sidewall, and a top face porous tissue ingrowth surface at least along a portion of said top face adjacent the passageway;
  (b) a transcutaneous conduit mated with said passageway such that, when the subcutaneous member is implanted, a proximal conduit end projects above the skin surface whereby a transcutaneous access channel extends from outside the skin surface into the body interior region, and a distal conduit end is adapted with a connection fitting that selectively enables the access channel to be extended into more remote regions of a living body by the connection of a second conduit component; and,
  (c) a conduit porous tissue ingrowth surface at least along a portion of the outer surface of the transcutaneous conduit that begins in the passageway and extends transcutaneously from beneath the top face of the upper wall, through the skin, to a point above the external skin surface when said subcutaneous member is implanted.

31. A medical apparatus according to claim 30 further wherein said subcutaneous member comprises a structure sized, shaped, and subcutaneously positioned to minimize movement of the porous tissue ingrowth surfaces while allowing the orientation of the conduit to be changed from a path generally parallel to the skin where the conduit is distal of the subcutaneous member to a path that intersects the skin surface when the conduit is proximal of the subcutaneous member.

32. A medical apparatus according to claim 30 further wherein said porous tissue ingrowth surfaces along the outer surface of said transcutaneous conduit extends from beneath the bottom face of the upper wall to a point above the external skin surface.

33. A medical apparatus according to claim 30 further wherein said subcutaneous member consists essentially of a material that is compatible with living dermal tissue.

34. A medical apparatus according to claim 30 further wherein said subcutaneous member consists essentially of a material that is compatible with living non-dermal tissue.

\* \* \* \* \*